United States Patent
Carmi (10) Patent No.: US 9,268,046 B2
(45) Date of Patent: Feb. 23, 2016

(54) IMAGING SYSTEM DETECTOR CALIBRATION

(75) Inventor: Raz Carmi, Haifa (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 109 days.

(21) Appl. No.: 14/129,720

(22) PCT Filed: Jul. 12, 2012

(86) PCT No.: PCT/IB2012/053565
§ 371 (c)(1),
(2), (4) Date: Dec. 27, 2013

(87) PCT Pub. No.: WO2013/008198
PCT Pub. Date: Jan. 17, 2013

(65) Prior Publication Data
US 2014/0140469 A1    May 22, 2014

Related U.S. Application Data

(60) Provisional application No. 61/506,816, filed on Jul. 12, 2011.

(51) Int. Cl.
*A61B 6/03* (2006.01)
*G01D 18/00* (2006.01)
*G01T 7/00* (2006.01)
*A61B 6/00* (2006.01)
*G01T 1/24* (2006.01)
*G01N 23/04* (2006.01)

(52) U.S. Cl.
CPC ................. *G01T 7/005* (2013.01); *A61B 6/032* (2013.01); *A61B 6/4007* (2013.01); *A61B 6/4233* (2013.01); *A61B 6/585* (2013.01); *G01N 23/046* (2013.01); *G01T 1/249* (2013.01)

(58) Field of Classification Search
CPC ...... A61B 6/032; A61B 6/4233; A61B 6/582; A61B 6/585
USPC .................................................. 378/9, 10, 207
See application file for complete search history.

(56) References Cited

U.S. PATENT DOCUMENTS

| | | | |
|---|---|---|---|
| 4,472,823 A | 9/1984 | Waltham | |
| 5,828,719 A * | 10/1998 | He et al. | 378/4 |
| 6,064,068 A | 5/2000 | Bartle | |
| 6,075,835 A * | 6/2000 | Acharya et al. | 378/4 |
| 7,224,763 B2 * | 5/2007 | Naidu et al. | 378/5 |
| 7,476,026 B2 * | 1/2009 | Braunstein | 378/207 |

(Continued)

*Primary Examiner* — Allen C. Ho (57) ABSTRACT

A system (100) includes a stationary gantry (102) and a rotating gantry (104), wherein the rotating gantry is rotatably supported by the stationary gantry. The rotating gantry (104) includes a primary source (110) that emits primary radiation and a detector array (116) having at least one row of detector elements (502) extending along a longitudinal axis. The primary source and the detector array are located opposite each other, across an examination region, and the primary radiation traverses a path (112) between the primary source and the detector array and through an examination region (106) and illuminates the at least one row of detector elements of the detector array, which detects the primary radiation. The system further includes a supplemental source (114), wherein the supplemental source is affixed to a non-rotating portion of the system and emits radiation that traverses a sub-portion of the path and illuminates the at least one row of detector elements of the detector array, which detects the secondary radiation.

24 Claims, 6 Drawing Sheets

(56) References Cited

U.S. PATENT DOCUMENTS

| | | | |
|---|---|---|---|
| 7,602,951 B2* | 10/2009 | Hsieh et al. | 382/128 |
| 7,873,144 B2 | 1/2011 | Luhta et al. | |
| 8,585,286 B2* | 11/2013 | Livne et al. | 378/207 |
| 8,958,524 B2* | 2/2015 | Subramanian et al. | 378/4 |
| 2004/0199065 A1 | 10/2004 | Braunstein | |
| 2007/0010731 A1 | 1/2007 | Mistretta | |
| 2007/0145279 A1 | 6/2007 | Yanagita | |
| 2008/0217541 A1 | 9/2008 | Kim | |
| 2009/0161932 A1 | 6/2009 | Chen | |
| 2009/0161933 A1 | 6/2009 | Chen | |
| 2009/0175523 A1 | 7/2009 | Chen et al. | |
| 2010/0051816 A1 | 3/2010 | Snoeren et al. | |
| 2011/0012014 A1 | 1/2011 | Livne et al. | |

* cited by examiner

IMAGING SYSTEM DETECTOR CALIBRATION

CROSS-REFERENCE TO PRIOR APPLICATIONS

This application is the U.S. National Phase application under 35 U.S.C. §371 of International Application No. PCT/IB2012/053565, filed on Jul. 12, 2012, which claims the benefit of U.S Provisional Patent Application No. 61/506816, filed on Jul. 12, 2011. These application are hereby incorporated by reference herein.

FIELD OF THE INVENTION

The following generally relates to calibrating radiation sensitive detectors of an x-ray based imaging system detector array and is described with particular application to computed tomography (CT); however, the following is also amenable to other x-ray based imaging systems.

BACKGROUND OF THE INVENTION

A CT scanner generally includes an x-ray tube supported by a rotating gantry, which is rotatably affixed to a stationary gantry. The x-ray tube emits radiation that traverses an examination region and a portion of an object or subject therein. A subject support positions the object or subject in the examination region for scanning. A radiation sensitive detector array is disposed across the examination region, opposite the x-ray tube, and includes a plurality of detector elements that detects radiation traversing the examination region and produces projection data indicative of the detected radiation. The projection data can be reconstructed to generate volumetric image data indicative of the portion of the object or subject in the examination region.

A conventional CT scanner typically includes integrating detectors, which typically include a scintillator array optically coupled to a photodiode array (e.g., of silicon photodiodes). Conventional CT scintillator are based, for example, on $Gd_2O_2S$ (referred to as GOS), $(LuTb)_3Al_5O_{12}$ (referred to as LuTbAG) or several forms of (Gd, Y, Ga)AG. The scintillator array includes scintillating material that absorbs x-rays that pass through the examination region and the portion of the object or subject and produces light in proportion to the total energy of the absorbed x-rays. The photodiode array absorbs the light produced by the scintillating material and converts the absorbed light into an electrical current in proportion to the light absorbed. The ideal detector produces a signal current in direct proportion to the x-ray intensity (i.e. the total energy of all photons in a reading) absorbed in the detector.

Such detectors have time dependent gains. Generally, the gain of a detector represents the transfer function from x-ray energy to an electric signal. Typically, the material selected for the scintillator of the detector array has a gain that is nearly constant over time. As such, an air calibration scan is performed to generate detector gain calibration data and subsequent air calibration scans can be made once every month or so to reflect changes in detector gain. Generally, an air calibration includes scanning with nothing located in the examination region so that the x-rays pass through the examination region without being attenuated and the gain of each detector is determined based on the output signal of the detectors. Any change in gain between calibrations typically may not be significant and has been neglected.

In some instances, the above-noted conventional CT detectors may not be the optimal choice or even appropriate, for example, for applications such as those involving spectral CT, photon counting, or protocols using very low detected x-ray flux. For such applications, detectors with higher gain (light output) or with spectral resolved properties is often the better choice. Scintillators with higher light output may be better suited since they offer a higher signal to noise ratio and reduced image artifacts in cases such as: 1) clinical protocols with low patient dose; 2) high speed scans (e.g., cardiac scans); 3) protocols with low tube voltage for high soft tissue contrast definition; 4) CT scanners having detector arrays with especially small pixels for high spatial resolution; 5) double-layer dual-energy CT for better material separation, and/or other advantages. Direct conversion materials may be the optimal choice for photon-counting spectral CT.

Several detector materials with higher light output (relative to GOS) are known. Examples of such materials include scintillator materials such as ZnSe (maximum (max.) ~80,000 photons/mega-electron volt (ph/MeV)), $Y_2O_2S$ (max. ~63,000 ph/MeV), $SrI_2$ (max. ~90,000 ph/MeV), $LaBr_3$ (max. ~61,000 ph/MeV), $Ba_2CsI_5$ (max. ~97,000 ph/MeV), etc., and direct conversion materials such as CdZnTe, CdTe, TlBr, GaAs, etc. For comparison, the conventional GOS scintillator can reach lower light output of max. ~50,000 photons/MeV. Several light-element scintillators such as the aforementioned ZnSe may be well-suited for double-layer dual-energy CT detectors. From the aspect of light photodetectors, silicon photomultipliers (SiPM) or avalanche photodiodes (APD) can be used to achieve higher sensitivity.

Unfortunately, the above noted materials have unstable that the gains change more frequently over time, relative to the gain of the aforementioned conventional scintillators. As such, conventional approaches for calibrating for gain with a conventional scintillator, such as the example approach discussed above in which the gain is re-calibrated every month or so, are not well suited to be used to calibrate the gain of such materials. Therefore, there is an unresolved need for other approaches for calibrating detectors for gain.

SUMMARY OF THE INVENTION

Aspects of the present application address the above-referenced matters and others.

According to one aspect, a system includes a stationary gantry and a rotating gantry, wherein the rotating gantry is rotatably supported by the stationary gantry. The rotating gantry includes a primary source that emits primary radiation and a detector array having at least one row of detector elements extending along a longitudinal axis. The primary source and the detector array are located opposite each other, across an examination region, and the primary radiation traverses a path between the primary source and the detector array and through an examination region and illuminates the at least one row of detector elements of the detector array, which detects the primary radiation. The system further includes a supplemental source, wherein the supplemental source is affixed to a non-rotating portion of the system and emits radiation that traverses a sub-portion of the path and illuminates the at least one row of detector elements of the detector array, which detects the secondary radiation.

In another aspect, a method includes performing an initial detector gain calibration procedure, which includes performing an air scan using a primary source that is also used to perform object or subject scans and performing a supplemental scan using a secondary source that is not used to perform the object or subject scans. The method further includes performing an object or subject scan, which includes scanning an object or subject using the primary source, and performing a subsequent supplemental scan using the supplemental source. The method further includes generating a signal in electronic format which is indicative of detector gain calibration data based on results of the initial detector gain calibration procedure and the subsequent supplemental scan.

In another aspect, a method includes obtaining air scan calibration data, for a detector array of an imaging system, which is generated based on an air calibration scan performed using a primary source, which is also used to scan an object or subject. The method further includes obtaining first calibration update data, for the detector array of the imaging system, which is generated based on a supplemental scan performed with a supplemental source, which is not used to scan the object or subject. The air scan calibration data and the first calibration update data are part of a same initial detector gain calibration procedure. The method further includes obtaining second calibration update data, for the detector array of the imaging system, which is generated based on a subsequent supplemental scan performed with the supplemental source. The method further includes obtaining data acquired while scanning the object or subject using the primary source. The second calibration update data and the data acquired are part of a same object or subject scan procedure. The method further includes generating detector gain calibration data based on the obtained air scan calibration data, the obtained first calibration update data and the obtained second calibration update data. The method further includes correcting the data acquired based on the generated detector gain calibration data.

Still further aspects of the present invention will be appreciated to those of ordinary skill in the art upon reading and understand the following detailed description.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
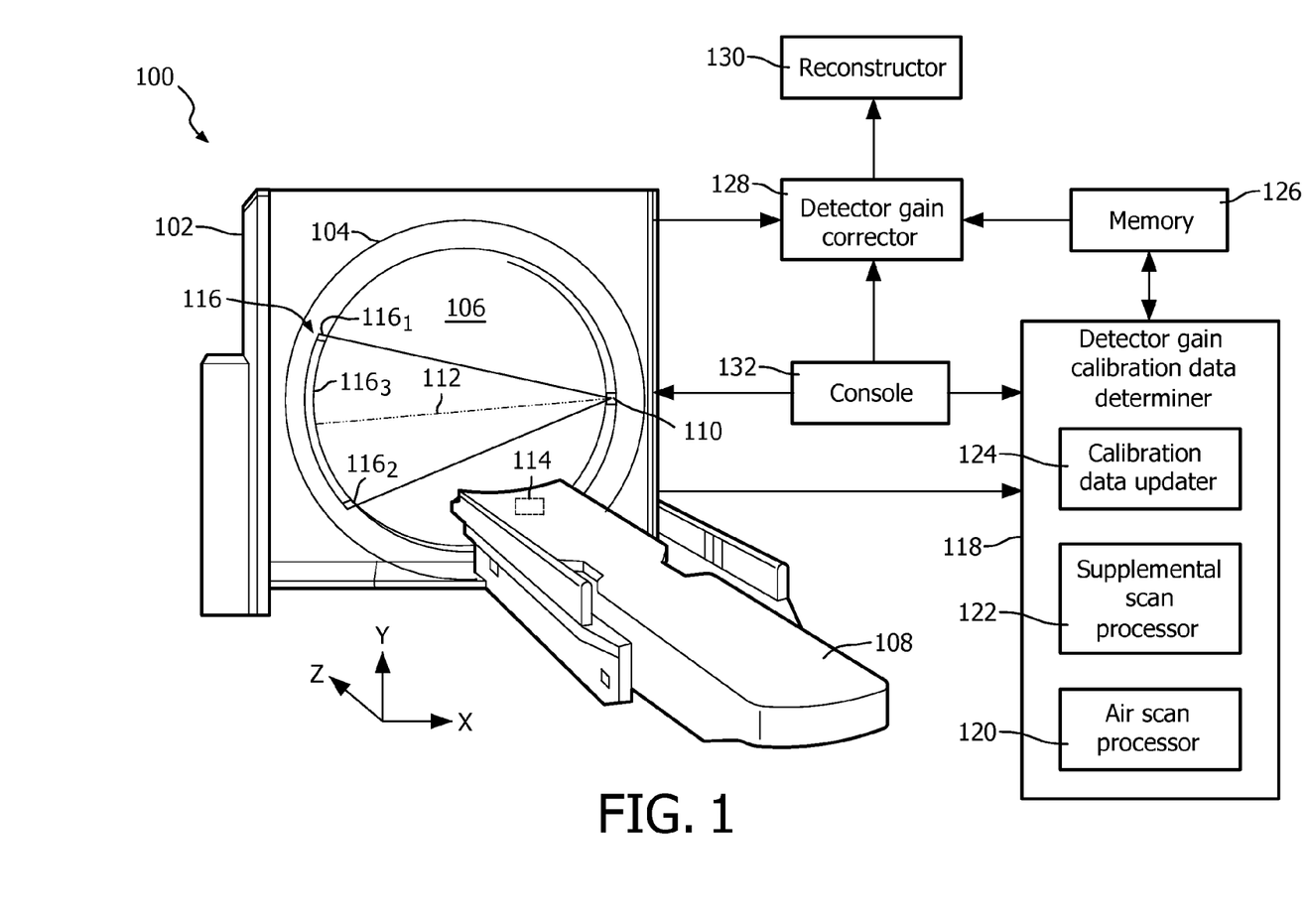
FIG. 1 schematically illustrates an example imaging system with a primary source, a supplemental source, and a detector gain calibration data determiner, which determines detector gain calibration data based on data acquired using both the primary and the supplemental sources.

FIG. 1 illustrates an imaging system 100 such as a computed tomography (CT) scanner.

The imaging system 100 includes a stationary gantry 102 and a rotating gantry 104, which is rotatably supported by the stationary gantry 102. The rotating gantry 104 is configured to rotate around an examination region 106 about a longitudinal or z-axis.

A subject support 108, such as a couch, supports an object or subject (human or animal) in the examination region 106 and positions the object or subject with respect to x, y, and/or z axes before, during and/or after scanning.

A primary source 110, such as an x-ray tube, is supported by the rotating gantry 104 and rotates in coordination with the rotating gantry 104 about the examination region 106. The primary source 110 emits a generally fan, cone, or wedged shaped radiation beam that traverses along a path 112 from one side of the examination region 106 to the other. The primary source 110 is used to perform a conventional air scan or an object or subject scan.

A primary radiation source 110, such as an x-ray tube, is supported by the rotating gantry 104 and rotates in coordination with the rotating gantry 104 about the examination region 106. The primary radiation source 110 emits a generally fan, cone, or wedged shaped radiation beam that traverses along a path 112 from one side of the examination region 106 to the other. The primary radiation source 110 is used to perform a conventional air scan or an object or subject scan.

A supplemental source 114 is affixed in the stationary gantry 102. In FIG. 1, the supplemental source 114 is located in a region that is below the subject support 108. As such, when the supplemental source 114 is actuated to emit radiation, the supplemental source 114 emits radiation that traverses only a sub-portion of the path 112. As described in greater detail below, the supplemental source 114 can be employed before, during, between and/or after an object or subject scan(s) performed with the primary radiation source 110 or after an air scan performed with the primary source 110.

A radiation sensitive detector array 116 is also supported by the rotating gantry 104 and is located opposite the primary radiation source 110, across the examination region 106 to the other side of the examination region 106. The detector array 116 includes one or more rows of detector elements, where each row extends along the x-direction, and the rows (where there are two or more) are arranged with respect to each other along the z-direction. The detector elements detect radiation (from the primary radiation source 110 and/or the supplemental source 114) traversing the at least part of the path 112 and generate projection data indicative thereof.

The detector array 116 includes outer detectors $116_1$ and $116_2$ and inner detectors $116_3$, which are located between the outer detectors $116_1$ and $116_2$. The outer detectors $116_1$ and $116_2$ each include one or more detectors having a generally stable gain (e.g., GOS detectors) in that the gain is nearly constant over time. The inner detectors $116_3$ include a material and/or detector technology with higher gain and/or other improved characteristics relative to the conventional detectors with the stable gain. Suitable materials include scintillating materials such as ZnSe, $Y_2O_2S$, $SrI_2$, $LaBr_3$, $Ba_2CsI_5$, and/or other scintillating material, direct conversion materials such as CdZnTe, CdTe, TlBr, GaAs, and/or other direct conversion material, and suitable technologies include silicon photomultipliers (SiPM), avalanche photodiodes (APD), and/or other detector technologies. Such materials and/or technologies tend to have unstable gains relative to conventional detectors, in that gain changes that impact image quality occur more frequently with respect to time relative to conventional detector.

A detector gain calibration determiner 118 determines detector gain calibration data for each object or subject scan. The illustrated detector gain calibration determiner 118 includes an air scan processor 120 that receives data acquired during a conventional air scan performed with the primary source 110 without and object or subject in the examination region 106 and generates air scan calibration data therewith. Any known or other approach can be used to generate the air scan calibration data.

A detector gain calibration determiner 118 determines detector gain calibration data for each object or subject scan. The illustrated detector gain calibration determiner 118 includes an air scan processor 120 that receives data acquired during a conventional air scan performed with the primary radiation source 110 without an object or subject in the examination region 106 and generates air scan calibration data therewith. Any known or other approach can be used to generate the air scan calibration data.

The detector gain calibration determiner 118 also includes a calibration data updater 124 that updates the air scan calibration data for a particular object or subject scan based on the calibration update data generated from a supplemental scan for the particular object or subject scan and calibration update data from a previous supplemental scan, producing the detector gain calibration data. In one instance, the calibration update data serves as a second-order correction in addition to air scan calibration data (e.g., a small correction relative to the primary correction). An example approach for generating the update data and producing the detector gain calibration data is discussed in greater detail below.

Memory 126 is used to store one or more of the detector gain calibration data, the calibration update data, and the air scan calibration data. The detector gain calibration determiner 118 can read from and write to the memory 126.

A detector gain corrector 128 corrects signals generated by the detector array 116 (or a detector array of another system) based on the detector gain calibration data in the memory 126. Any known or other approach can be used to correct the projection data based on the detector calibration data. An example approach for correcting the project data is discussed in greater detail below.

A reconstructor 130 reconstructs the corrected projection data and generates volumetric image data indicative of the examination region 106 and a portion of the object or subject therein. An example approach for reconstructing the corrected projection data is discussed in greater detail below. The reconstructed image data can be further processed to generate one or more images of the portion of the object or subject which can be filmed, visually presented, saved, and/or otherwise processed.

A general purpose computing system serves as an operator console 132, and includes an output device such as a display and an input device such as a keyboard, mouse, and/or the like. In the illustrated embodiment, the console 132 is configured to control the imaging system 100, for example, to perform an air calibration scan (with the primary radiation source 110), a supplemental scan (with the supplemental source 114) and/or an object or subject scan (with the primary radiation source 110), actuate the detector gain calibration determiner 118, actuate the detector gain corrector 128, and/or otherwise control the imaging system 100.

It is to be appreciated that the detector gain calibration determiner 118 and/or the detector gain corrector 128 can be implemented via one or more processor executing one or more computer executable instructions embedded on computer readable storage medium such as physical memory. Additionally or alternatively, at least one of the computer executable instructions is carried by a signal or carrier wave. Moreover, the detector gain calibration determiner 118 and/or the detector gain corrector 128 can be local or remote to the imaging system 100 and/or part of the console 132 and/or one or more other computing device.

Figure 2:
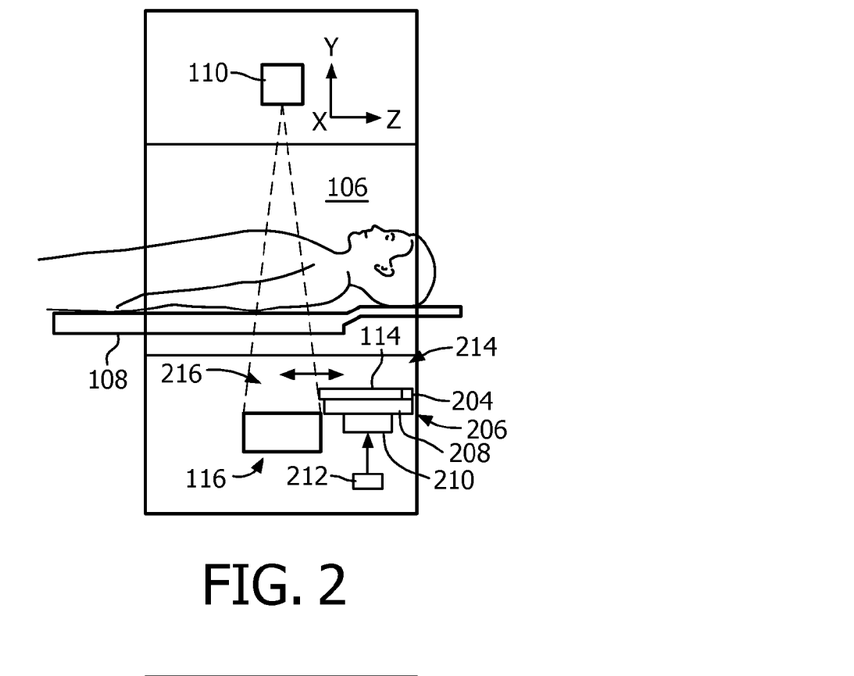
FIGS. 2 and 3 schematically illustrate an example of the supplemental source looking into the system along the x-direction.
Figure 3:
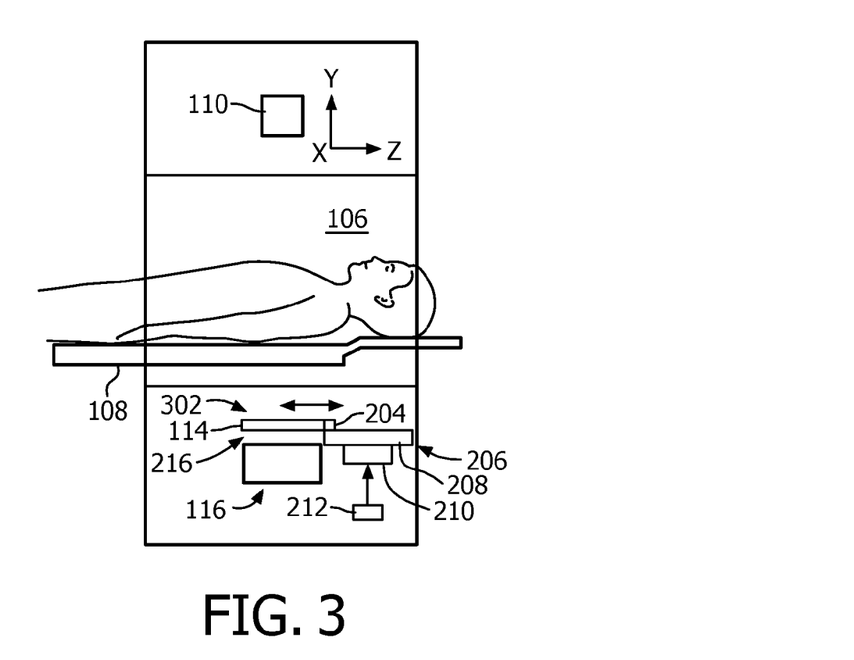
Figure 4:
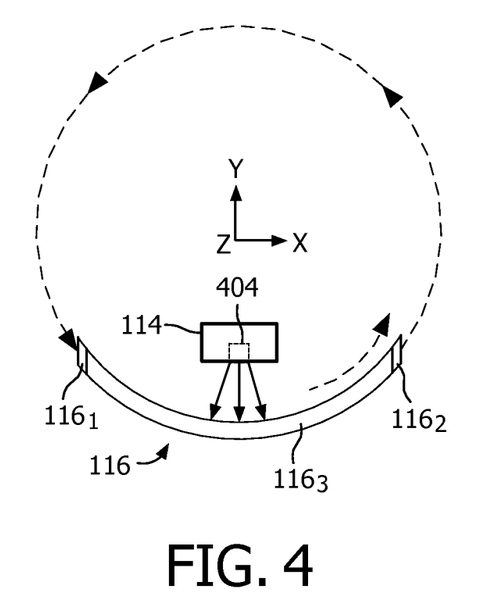
FIG. 4 schematically illustrates the example of the supplemental source looking into the system along the z-direction.
Figure 5:
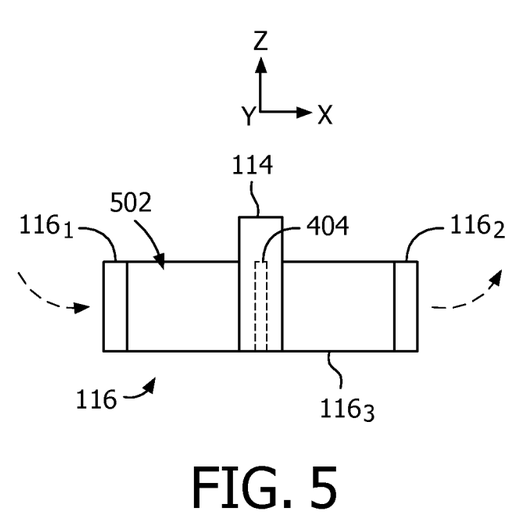
FIG. 5 schematically illustrates the example of the supplemental source looking into the system along the y-direction.

FIGS. 2, 3, 4 and 5 schematically illustrate a non-limiting example of the supplemental source 114 in connection with the imaging system 100. FIGS. 2 and 3 schematically illustrate side views of the imaging system 100 looking into the imaging system 100 from the x-direction, FIG. 4 schematically illustrates a view looking into the examination region 106 from the z-direction, and FIG. 5 schematically illustrates a view looking down from primary radiation the source 110 into the detector array 116 from the y-direction.

Initially referring to FIGS. 2 and 3, the supplemental source 114 is affixed to a moveable portion 204 of a bearing 206. A stationary portion 208 of the bearing 206 is affixed in the imaging system 100. A drive mechanism 210 is configured to move the moveable portion 204 of the bearing 206 and hence the supplemental source 114. Suitable bearings include, but are not limited to, a linear slide, ball, roller, and/or other bearing. Suitable drive mechanisms include, but are not limited to, a belt, chain, lead screw, ball screw, two or more gears, etc., and a motor. Other approaches, including a combination of the above, are also contemplated herein.

A controller 212 is configured to control the drive mechanism 208 to move the supplemental source 114 via the bearing 206, for example, between at least two positions, including a first or retracted position 214 (FIG. 2) in which the supplemental source 114 is not located in a region 216 between the subject support 108 and the detector array 116, and a second or extended position 302 (FIG. 3) in which the supplemental source 114 is located in the region 216 between the subject support 108 and the detector array 116. In this example, the supplemental source 114 is positioned in the retracted position 214 (FIG. 2) when scanning an object or subject and in the extended position 302 (FIG. 3) for performing a supplemental scan.

In FIGS. 4 and 5, the supplemental source 114 is in the extended position 302 (FIG. 3) and activated to emit x-ray radiation. As shown in FIG. 4, the supplemental source 114 extends in the x-direction only over a sub-portion of the length of the inner detectors $116_3$. As shown in FIG. 5, the supplemental source 114 extends in the z-direction at least the entire z-axis width of the detector array 116. The detector array 116 rotates as the supplemental source 114 emits x-ray radiation, and the radiation emitted by the supplemental source 114 sequentially illuminates, column by column, all the detectors elements of the detector array 116, including the outer detector $116_1$, the inner detectors $116_3$, and the outer detectors $116_2$.

In FIGS. 4 and 5, the detector array 116 has the shape of a matrix of pixels 502 (FIG. 5) on the surface of an arc (FIG. 4). The detector array 116 has geometry of about ten (10) centimeters (cm) wide along the z-direction and about one hundred (100) cm along the arc or x-direction. In other embodiments, the detector array 116 is wider or narrower and/or longer or short. The geometry and pixel size of the outer detectors $116_1$ and $116_2$ and the inner detectors $116_3$ are the same, and the location of the outer detectors $116_1$ and $116_2$ with respect to the inner detectors $116_3$ is the same. In other embodiments, geometry and pixel size and/or the locations may be different.

In FIGS. 4 and 5, the supplemental source 114 is a line source with an array 404 of emitting regions spatially distributed along a longitudinal axis. The line source 114 is spatially oriented with respect to the detector array 116 such that the longitudinal axis of the line source is transverse to the longitudinal axis of the detector array 116. An example of a suitable line source includes, but is not limited to, a carbon nanotube (CNT) x-ray source. Carbon nanotubes generally are good electron field emitters due to their high aspect ratio, superior electrical and thermal conductivity, and relatively high chemical and mechanical stability.

With CNTs, the x-ray tube current is generated by applying an external electrical field to extract the electrons from the CNTs. By varying the extraction electrical field, x-ray radiation with programmable waveforms can be readily generated and gated with physiological signals or others. Spatially distributed x-ray source arrays with one-and two-dimensionally distributed focal spots are constructed by using matrix addressable multi-pixel CNT cathode. Switching, scanning, and regulating the x-ray beams can be achieved through gate control electronics.

Carbon nanotube cold cathodes are also relatively easy to make, either by chemical vapor deposition in situ growth or by post-growth transfer onto a substrate. A line-shaped x-ray source can be fabricated using field emission x-ray source technology. The cathode can be made by CNT technology or otherwise with an array of micro-machined field emission tips. By doing so, it is possible to obtain very sharp tips and very close proximity between the tips and the gate electrode. This greatly reduces the potential difference between the tip and the gate required to achieve the field emission.

The array 404 of emitting regions may be very densely packed. As a result, even though the current that can be obtained from a single tip is small, the total current that can be obtained from an array can be much larger. Using the technique as described above, a line-shaped x-ray source can be fabricated. The width can be made as narrow as one hundredth (0.01) of a millimeter (mm) or less, and the length of the source can be made in tens of centimeters or longer. The array of emitters of the radiation source 114 may or may not produce a homogenous beam along the long axis (z-direction) of the radiation source 114.

In one non-limiting instance, the line source has: 1) temporal stability over about one (1) second.; 2) spatial uniformity on a length of about one (1) mm; 3) an intensity or the power on the order of magnitude of micro Amperes of source current, while using an electron accelerating voltage in the order of 100 kV. Such low power is sufficient because the source is very close (e.g., few centimeters) to the detector array 110; 4) an x-ray spectrum in a range of the spectrum produced by standard x-ray tube operated in 80-140 kV (however, it is not required that the spectrum will be completely identical to the primary source 108).

Figure 6:
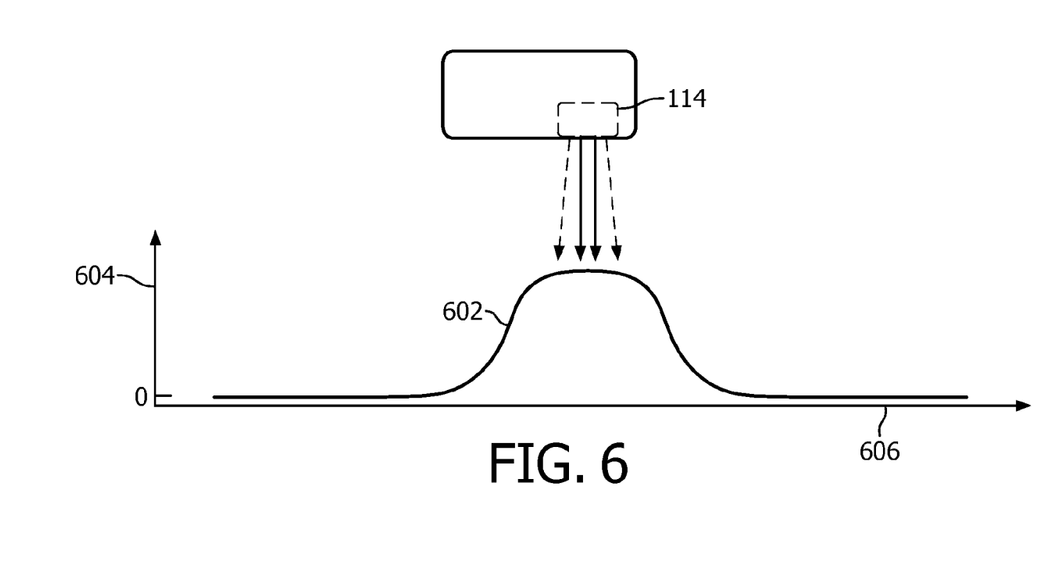
FIG. 6 illustrates an example profile of x-ray intensity on a detector element from the supplemental source as a function of the detector array rotation angle with respect to the supplemental source.
Figure 7:
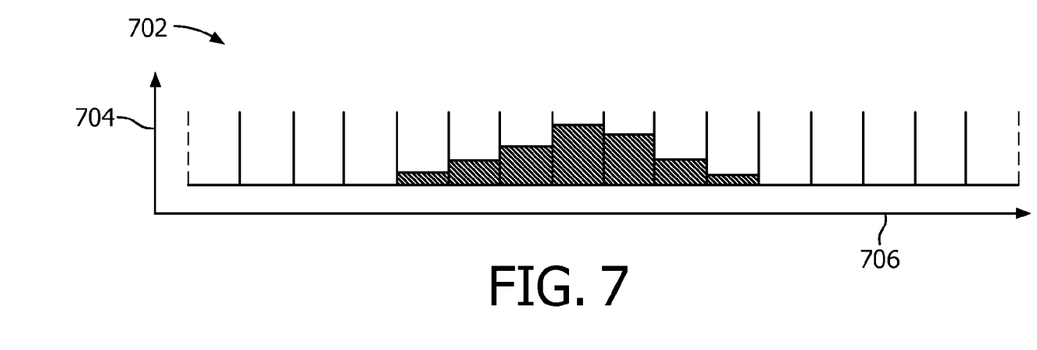
FIG. 7 illustrates an example profile of the signal output by the detector element of FIG. 6 as a function of integration period for the detector element.

FIG. 6 shows a profile 602 of radiation intensity of the line source on a single detector element as a function of rotation angle of the detector array 116 with respect to the line source, wherein a y-axis 604 represents intensity and an x-axis 606 represents rotation angle. FIG. 7 shows a profile 702 of the output signal of the detector element of FIG. 6 as a function of integration period for the detector element, wherein a y-axis 704 represents signal level and an x-axis 706 represents integration period.

As shown in FIGS. 6 and 7, the profiles 602 and 702 start from a low value, increase to a maximum, and then decrease to a low value. Various approaches can be used to determine a value to use for calibration purposes. In one instance, a maximum signal is estimated when the detector pixel passes beneath the source. This can be done for example by interpolation between the five highest readings. A second approach is to sum all readings which are above a pre-defined noise threshold. A third approach is to simply take the highest reading signal. Other approaches are also contemplated herein.

Variations are contemplated.

Figure 8:
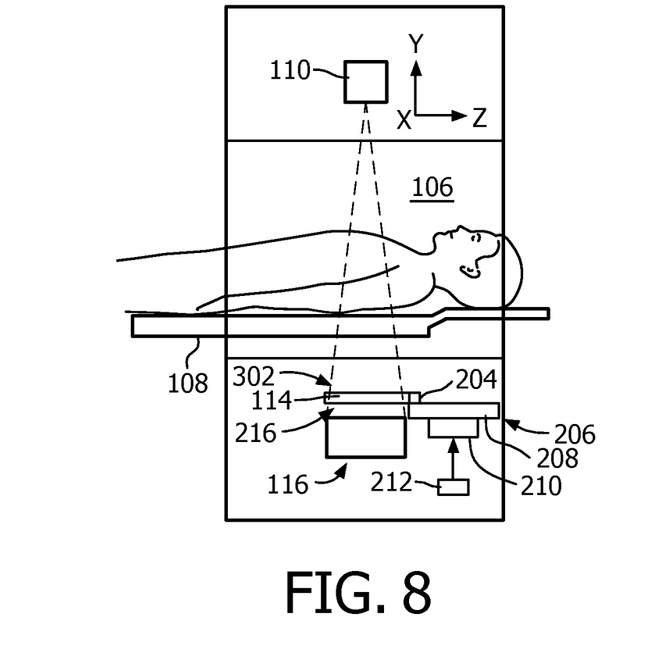
FIGS. 8 and 9 schematically illustrate non-limiting variations of supplemental source in the system.

FIG. 8 schematically illustrates a variation in which the supplemental source 114 is in the path of the beam from the primary source 110 while the primary source 110 emits radiation. In FIG. 8, the supplemental source 114 is moved to the extended position 302 as described herein and left there while scanning the object or subject. This variation can be used for undersampled acquisitions where rays passing through the supplemental source 114 can be ignored or discarded.

Figure 9:
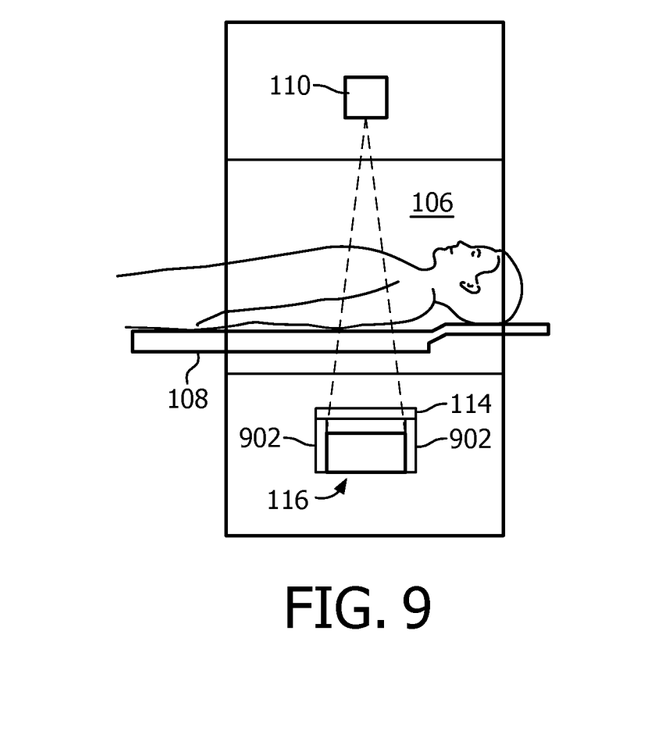

FIG. 9 schematically illustrates another variation in which the supplemental source 114 is located at static position. In FIG. 9, the supplemental source 114 is stationarily affixed at the extended position 302 via brackets 902. Likewise, this embodiment can be used for undersampled acquisitions where rays passing through the supplemental source 114 can be ignored or discarded.

In the variations illustrated in FIGS. 8 and 9, an appropriate image reconstruction technique is used. A suitable reconstruction technique is a reconstruction technique that can deal with undersampled projections such as a statistical iterative reconstruction technique, compressed sensing methods, and/or known image reconstruction technique. Examples of suitable reconstruction techniques can be found at least in US patent application publication 20090175523 ("Method for image reconstruction using sparsity-constrained correction"), US patent application publication 20090161933 ("Method for dynamic prior image constrained image reconstruction"), US patent application publication 20090161932 ("Method for prior image constrained image reconstruction"), and US patent application publication 20070010731 ("Highly constrained image reconstruction method").

In another variation, the secondary radiation source 114 is not located in the stationary gantry 102 between the support 108 and detector array 106. For example, the secondary radiation source 114 can alternatively be located in the subject support 108, affixed to the outside cover of the stationary gantry 102 within the aperture and over the region where x-rays emitted by the primary source 110 traverse to illuminate the detector array 116, and/or other regions.

Figure 10:
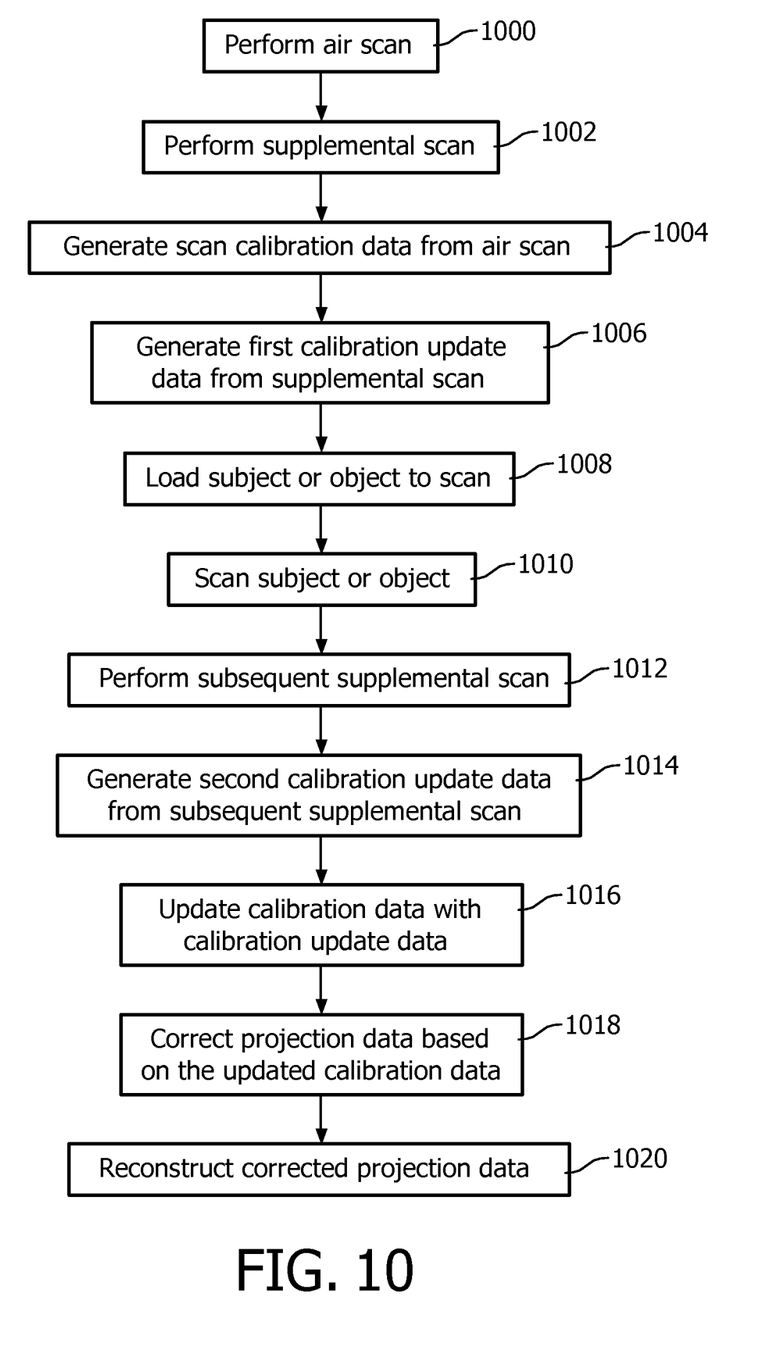
FIG. 10 illustrates an example method for gain calibrating the detector array of the imaging system.

FIG. 10 schematically illustrates example method of gain calibrating the detector array 116. For this example, the imaging examination includes a plurality of scans.

It is to be appreciated that the ordering of the below acts is for explanatory purposes and not limiting. As such, other orderings are also contemplated herein. In addition, one or more of the acts may be omitted and/or one or more other acts may be included.

At 1000, an air scan is performed. As described herein, the primary source 110 is used to perform air scans.

At 1002, a supplemental scan is performed. As described herein, the supplemental source 114 is used to perform supplemental scans.

It is to be appreciated that the combination of acts 1000 and 1002 can be considered as performing an initial detector gain calibration procedure.

At 1004, air scan calibration data is generated for the air scan for both the inner detectors $116_3$ (with the less stable detectors) and the outer detectors $116_1$ and $116_2$.

At 1006, first calibration update data is generated for both the inner detectors $116_3$ and the outer detectors $116_1$ and $116_2$.

At 1008, an object or subject is positioned in the examination region 106 for a scan.

At 1010, the object or subject is scanned. As described herein, the primary source 110 is used to perform object or subject scans.

At 1012, a supplemental scan is performed in connection with the object or subject scan.

It is to be appreciated that the combination of acts 1010 and 1012 are part of a same object or subject scan procedure.

At 1014, second calibration update data is generated for both the inner detectors $116_3$ and the outer detectors $116_1$ and $116_2$.

At 1016, the air scan calibration data is updated based on the first and second calibration update data.

At 1018, projection data from the scan of the object or subject is corrected based on the detector gain calibration data.

At 1020, the corrected projection data is reconstructed, generating volumetric image data of the object or subject.

Additionally or alternatively, act 1012 can be performed before or concurrently with act 1010.

Where the imaging exam includes more than one scan, acts 1008 to 1020 are repeated for each scan. Where a subsequent scan is performed with the object or subject at a different z-axis location, the object or subject can be moved before, during and/or after performing a supplemental scan.

The above may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

The following provides an example of generating air scan calibration data, calibration update data and detector gain calibration data (via the detector gain calibration data determiner 118), correcting projection data with the detector gain calibration data (via the detector gain corrector 128), and reconstructing the corrected projection data (via the reconstructor 130).

Generally, the behavior of attenuated radiation in a scanned object or subject can be characterized as shown in EQUATION 1:

$$I = I_0 e^{-\int \mu(x) dx}, \quad \text{EQUATION 1:}$$

where I is the radiation intensity of an x-ray incident on a single detector element after traversing the portion of an object or subject in the examination region 106, $I_0$ is the radiation intensity of the x-ray before traversing the portion of an object or subject therein, and $\mu(x)$ is the local radiation attenuation of the x-ray in the object or subject.

Signals S and $S_0$ are assumed to be proportional to the radiation intensities I and $I_0$ by a constant gain factor G, as shown in EQUATIONS 2 and 3:

$$S = G \cdot I, \text{ and} \quad \text{EQUATION 2:}$$

$$S_0 = G \cdot I_0. \quad \text{EQUATION 3:}$$

Based on EQUATIONS 1-3, if the detector gain is constant, the attenuation line integral P can be determined based on EQUATION 4:

$$p = \int \mu(x) dx \quad \text{(EQUATION 4)}$$
$$= -\ln\left(\frac{I}{I_0}\right)$$
$$= -\ln\left(\frac{S}{S_0}\right)$$
$$= \ln(S_0) - \ln(S),$$

and if the detector gain varies from the time of the air scan to the time of the object or subject scan, the attenuation line integral P is determined based on EQUATION 5:

$$p = \int \mu(x) dx \quad \text{(EQUATION 5)}$$
$$= \ln\left(\frac{S_0}{G}\right) - \ln\left(\frac{S}{G'}\right)$$
$$= \ln\left(S_0 \cdot \frac{G'}{G}\right) - \ln(S).$$

From EQUATION 5, in order to solve for $$P, S'_0 = S_0 \cdot \frac{G'}{G}$$

is determined.

The relation between the signals of a particular scan to the data from the air scan is given by EQUATION 6:

$$S_0 = S_0^m \cdot k, \quad \text{EQUATION 6:}$$

where $S_0^m$ is the signal from the air scan, which is performed using the primary source 110, and k is a ratio of the tube current of the object or subject scan to the tube current of the air scan.

The air scan processor 120 processes the data from the air scan and stores $S_0^m$ for each detector element in the memory 126. The x-ray tube current value that was used during the air calibration is also stored in the memory 126 and is used to calculate the ratio k automatically for each object or subject scan.

A supplemental scan, using the supplemental source 114, measures $S_c^m$ and $S_r^m$, where $S_c^m$ is the signal of an unstable detector pixel (from inner detectors $116_3$) and $S_r^m$ is the signal of a stable detector pixel (from outer detectors $116_1$ or $116_2$), or a weighting of the two outer detectors $116_1$ and $116_2$, in a same detector row. The supplemental scan processor 122 process the data from the supplemental scan and stores in these measurements the memory 126.

As part of an imaging examination of an object or subject, another or subsequent supplemental scan(s) is performed (using the supplemental source 114) before, during, between and/or after an object or subject scan (using the primary source 110), measuring $S_c^n$ and $S_r^n$. The supplemental scan processor 122 process the data from the subsequent supplemental scan and stores the corresponding measurements in the memory 126.

From the stored measurements, $S_c^n$ is corrected based on EQUATION 7:

$$S_c^{n'} = S_c^n \cdot \frac{S_r^m}{S_r^n} \quad \text{EQUATION 7}$$

where $S_c^{n'}$ is the corrected $S_c^n$ with respect to any changes in the distributed line-source from the time of the previous supplemental scan.

The calibration data updater 124 corrects the air scan calibration data based on EQUATION 8:

$$S_0^{m'} = S_0^m \cdot \frac{S_c^{n'}}{S_c^m} \qquad \text{EQUATION 8}$$

$$= S_0^m \cdot S_c^n \cdot \frac{S_r^m / S_r^n}{S_c^m}.$$

The detector gain calibration determiner 118 updates the detector gain calibration data stored in the memory 126 by replacing the previous values $S_0^m$ (for each detector pixel) with the new values $S_0^{m'}$.

The detector gain corrector 128 corrects a signal of an object or subject scan through: EQUATION 9:

$$S_0' = S_0^{m'} \cdot k \qquad \text{EQUATION 9}$$

$$= k \cdot S_0^m \cdot S_c^n \cdot \frac{S_r^m / S_r^n}{S_c^m}.$$

The reconstructor 130 can determined the line integral for the corrected signal based on EQUATION 10:

$$P = \int \mu(x) dx = \ln(S_0') - \ln(S). \qquad \text{EQUATION 10:}$$

Note that the result is independent of the exact intensities and distribution of the distributed x-ray source because the intensity during the routine 'm' is canceled in the component $(S_r^m / S_c^m)$ and the intensity during the routine 'n' is canceled by the component $(S_c^n / S_r^n)$ in equations 8 and 9.

It is to be appreciated that that the foregoing provides a practical solution for calibrating unstable detectors, for example, during advanced clinical protocols in which the patient stays on the scanner table for a relatively long time such as in cases of multiple scans for perfusion studies or for interventional procedures. It may also enable repeated calibration between patients when a technician or other staff members are inside the CT room and there is a concern that the technician or other staff members will be exposed to ionizing radiation if the primary x-ray tube is operated during a standard air calibration procedure.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention claimed is:

1. A system, comprising:
a stationary gantry;
a rotating gantry, wherein the rotating gantry is rotatably supported by the stationary gantry, the rotating gantry, including:
a primary source that emits primary radiation; and
a detector array having at least one row of detector elements extending along a longitudinal axis,
wherein the primary source and the detector array are located opposite each other, across an examination region, and the primary radiation traverses a path between the primary source and the detector array and through the examination region and illuminates the at least one row of detector elements of the detector array, which detects the primary radiation; and
a supplemental source, wherein the supplemental source is affixed in the stationary gantry and emits radiation that traverses a sub-portion of the path and illuminates the at least one row of detector elements of the detector array, which detects a secondary radiation.

2. The system of claim 1, wherein the supplemental source is a line source with an array of radiation emitting regions spatially distributed along a longitudinal axis of the line source.

3. The system of claim 2, wherein the line source is spatially oriented with respect to the detector array such that the longitudinal axis of the line source is transverse to the longitudinal axis of the detector array.

4. The system of claim 2, wherein the line source sequentially illuminates the at least one row of detector elements as the detector array rotates through a path passed the supplemental radiation source.

5. The system of claim 1, wherein the supplemental source is configured to move between a first position in which the supplemental source is in the path between the primary source and the detector array and a second position in which the supplemental source is outside of the path between the primary source and the detector array, and wherein the supplemental source is actuated to emit radiation only when the supplemental source is in the second position.

6. The system of claim 1, wherein the supplemental source is configured to emit continuous, non-pulsed radiation.

7. The system of claim 1, further comprising:
a subject support configured to position structure to be scanned in the examination region for scanning, wherein the supplemental source is located between the subject support and the detector array.

8. The system of claim 1, the detector array, comprising:
first and second outer detectors of the at least one row of detector elements having first gain; and
inner detectors of the at least one row of detector elements having second gain and located between the first and second outer detectors, wherein the first gain is more stable with respect to time than the second gain.

9. The system of claim 1, further comprising:
a detector gain calibration determiner (118) that determines a detector gain calibration data for the detector array based on data acquired using the primary source during an air scan and data acquired using the supplemental source.

10. The system of claim 9, the detector gain calibration data determiner, comprising:
an air scan processor that generates air scan calibration data based on the data acquired using the primary source;
a supplemental scan processor that generates first calibration update data based on first data acquired using the supplemental source in connection with the air scan and second calibration update data based on second data acquired using the supplemental source in connection with an object or subject scan; and
a calibration data updater that updates the air scan calibration data based on the first and second calibration update data, generating detector gain calibration data.

11. The system of claim 10, wherein the first and second calibration update data update the air scan calibration data to take into account gain changes in the detector array.

12. The system of claim 10, further comprising:
a detector gain corrector that corrects projection data acquired during the object or subject scan with the generating detector gain calibration data, producing corrected projection data; and
a reconstructor that reconstructs the corrected projection data, producing volumetric image data.

13. The system of claim 9, wherein the supplemental source is actuated to emit radiation with an object or subject in the examination region.

14. The system of claim 9, wherein the supplemental source is actuated to emit radiation concurrently while the primary source is used to perform an object or subject scan.

15. A method, comprising:
performing an initial detector gain calibration procedure, which includes performing an air scan using a primary source that is also used to perform object or subject scans and performing a supplemental scan using a secondary source that is not used to perform the object or subject scans;
performing an object or subject scan, which includes scanning an object or subject using the primary source, and performing a subsequent supplemental scan using the supplemental source; and
generating a signal in electronic format which is indicative of detector gain calibration data based on results of the initial detector gain calibration procedure and the subsequent supplemental scan.

16. The method of claim 15, further comprising:
generating air scan calibration data based on the air scan;
generating calibration update data based on the supplemental scan and the subsequent supplemental scan; and
generating the signal based on the air scan calibration data and the calibration update data.

17. The method of claim 15, further comprising:
correcting projection data acquired via the object or subject scan, thereby producing corrected projection data; and
reconstructing the corrected projection data, thereby generating volumetric image data indicative of the object or subject.

18. The method of claim 15, wherein performing a subsequent supplemental scan comprises performing the subsequent scan with the object or subject in an examination region in which the object or subject scan is performed.

19. The method of claim 18, wherein performing a subsequent supplemental scan comprises performing the subsequent supplemental scan concurrently with the object or subject scan of the object or subject in the examination region.

20. The method of claim 15, further comprising:
moving the supplemental source to a scanning position to perform the subsequent supplemental scan; and
moving the supplemental source to a non-scanning position to perform the object or subject scan using the primary source.

21. The method of claim 15, wherein the supplemental source is a line source with a plurality of emitting regions distributed along a long axis of the line source.

22. The method of claim 15, further comprising:
actuating the supplemental source to emit non-pulsed radiation to perform the subsequent supplemental scan.

23. The method of claim 15, further comprising:
actuating the supplemental source to emit radiation while re-positioning the object or subject for a subsequent scan.

24. A method, comprising:
obtaining air scan calibration data, for a detector array of an imaging system, which is generated based on an air calibration scan performed using a primary source, which is also used to scan an object or subject;
obtaining first calibration update data, for the detector array of the imaging system, which is generated based on a supplemental scan performed with a supplemental source, which is not used to scan the object or subject;
wherein the air scan calibration data and the first calibration update data are part of a same initial detector gain calibration procedure;
obtaining second calibration update data, for the detector array of the imaging system, which is generated based on a subsequent supplemental scan performed with the supplemental source;
obtaining data acquired while scanning the object or subject using the primary source;
wherein the second calibration update data and the data acquired are part of a same object or subject scan procedure;
generating detector gain calibration data based on the obtained air scan calibration data, the obtained first calibration update data and the obtained second calibration update data; and
correcting the data acquired based on the generated detector gain calibration data.

* * * * *